(12) United States Patent
Jones et al.

(10) Patent No.: US 10,872,515 B2
(45) Date of Patent: Dec. 22, 2020

(54) METHOD AND APPARATUS FOR MONITORING AND REPORTING SALT LEVEL IN A WATER SOFTENER

(71) Applicants: Lee R. Jones, Batesville, IN (US); Kenneth C. Andrews, South Bend, IN (US)

(72) Inventors: Lee R. Jones, Batesville, IN (US); Kenneth C. Andrews, South Bend, IN (US)

( * ) Notice: Subject to any disclaimer, the term of this patent is extended or adjusted under 35 U.S.C. 154(b) by 0 days.

(21) Appl. No.: 16/174,342

(22) Filed: Oct. 30, 2018

(65) Prior Publication Data

US 2020/0279468 A1    Sep. 3, 2020

(51) Int. Cl.
| | |
|---|---|
| *G08B 21/00* | (2006.01) |
| *G08B 21/18* | (2006.01) |
| *G01N 27/22* | (2006.01) |
| *G01N 33/18* | (2006.01) |
| *H04L 29/08* | (2006.01) |
| *C02F 1/42* | (2006.01) |

(52) U.S. Cl.
CPC ......... *G08B 21/182* (2013.01); *G01N 27/226* (2013.01); *G01N 33/1886* (2013.01); *H04L 67/12* (2013.01); *H04L 67/26* (2013.01); *C02F 1/42* (2013.01); *C02F 2209/008* (2013.01); *C02F 2209/05* (2013.01); *C02F 2303/16* (2013.01)

(58) Field of Classification Search
CPC .... G08B 21/182; G08B 25/10; G01N 27/226; G01N 33/1886; H04L 67/12; H04L 67/26; C02F 2303/16; C02F 1/42; C02F 2209/008; C02F 2209/05; C02F 1/687; C02F 2209/42; C02F 2307/12; G01F 23/265; G01F 23/603; G01F 23/263; H04W 4/02; H04W 4/14
USPC ....... 340/612, 500, 618, 620, 617, 616, 619; 73/61.48, 293
See application file for complete search history.

(56) References Cited

U.S. PATENT DOCUMENTS

| | | | | |
|---|---|---|---|---|
| 5,132,669 | A * | 7/1992 | Jackson | G01F 23/0015 200/61.21 |
| 6,696,966 | B2 * | 2/2004 | Bearak | C02F 1/42 200/61.2 |
| 6,783,684 | B2 * | 8/2004 | Teel, Jr. | C02F 1/42 210/190 |
| 10,497,248 | B2 * | 12/2019 | Wanie | H04W 4/02 |
| 2008/0047881 | A1 | 2/2008 | Buck et al. | |

* cited by examiner

*Primary Examiner* — Anh V La
(74) *Attorney, Agent, or Firm* — Botkin & Hall, LLP

(57) ABSTRACT

A system for monitoring the level or amount of salt within a water softener brine tank is provided. The system includes a detection apparatus that uses at least three sensors that each measure the capacitance measured through the wall of a salt brine tank. The presence of salt adjacent a sensor causes the capacitance to increase and the sensor to report a salt present condition. Each sensor reports to a controller that will combine the signals from the sensors to detect when the level of the container is below a predetermined level. When at least one or more sensors report the salt level is below the predetermined level, the controller generates a push notification or an audio and/or visible alarm to alert the user the water softener tank needs to be replenished.

18 Claims, 5 Drawing Sheets

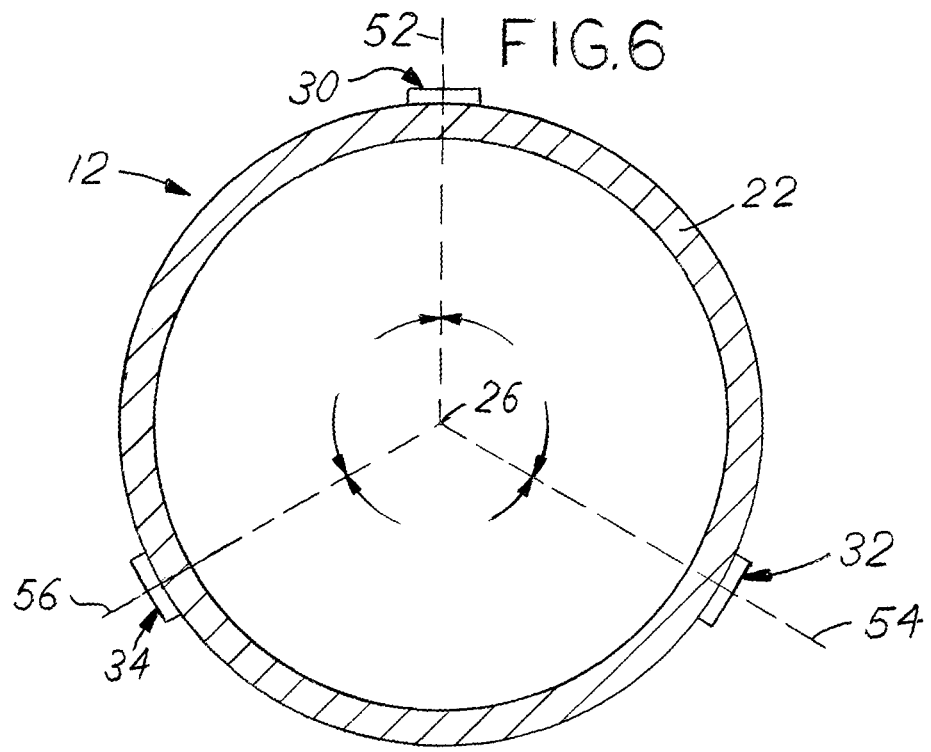
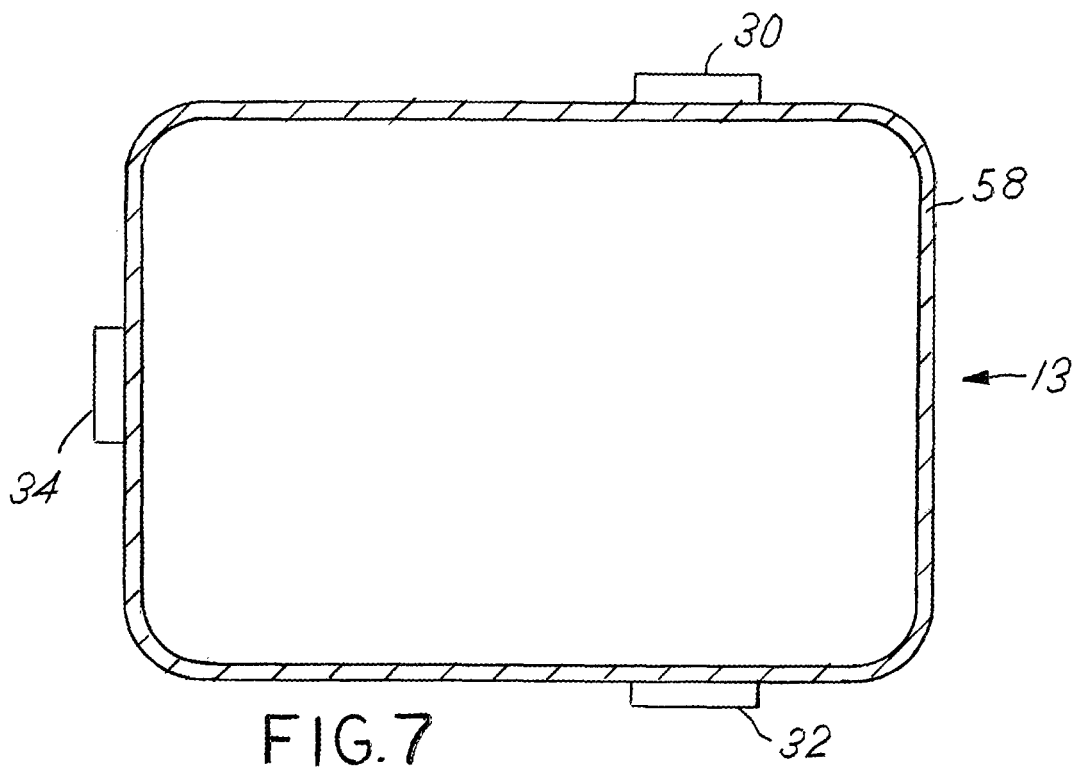

METHOD AND APPARATUS FOR MONITORING AND REPORTING SALT LEVEL IN A WATER SOFTENER

BACKGROUND OF THE INVENTION

The present invention relates to water softener salt tanks, and more specifically to a device which periodically monitors the level of the salt contained within the tank and activates an alarm or alert when a predetermined low level of salt is reached within the tank.

Water softeners are used to soften hard water prior to the water being utilized in a home, office, or industrial complex. The water softener includes a salt tank through which water and salt form a brine solution which is used to flush the resin bed of the water softener, removing contaminants from the bed.

During operation of the water softener, the salt contained in the water softener salt tank is depleted over time, such that the salt needs to be replenished to maintain the effectiveness of the water softener. However, due to the common remote placement of water softeners within a home, office or industrial complex, i.e., often in an area not commonly visited by people, and the opaque materials utilized to form the tanks in which the salt is contained, many times the salt in the water softener salt tank is unknowingly completely exhausted, such that it can no longer form a brine solution and the water used thereafter by an individual is "hard."

To remedy this problem, several different monitoring devices for water softener salt tanks have been developed. Many of these mechanisms involve a number of interacting parts which, when the salt reaches a predetermined lower limit in the tank, operate to provide some type of indication to a user that the salt in the water softener tank needs to be replenished. While most of these devices are sometimes effective in providing an indication to an individual when salt in a water softener tank needs to be replenished, the costs for assembly and/or maintenance of these prior art monitoring devices are often high due to the large number of interacting or interconnected components of the devices which do not hold up well under the harsh conditions formed by the salt water present in the water softener tank. The devices are also difficult to install for the average user and may interfere with refilling the tank with salt.

One prior art example used an external non-contact sensor but failed to cover the situation of a salt build up in front of the sensor while the rest of the tank is empty. It also failed to cover the possibility of a person, animal, or even an inanimate object coming close to the external case of the sensor thereby tripping the sensor to think the softener tank was full when it is empty.

Therefore, it is desirable to develop a monitoring device for a water softener salt tank that is not constructed from a large number of parts, and that is capable of accurately determining the amount of salt remaining in the water softener salt tank and is more easily installed outside the harsh environment of the tank. It is also desirable to develop a monitoring device which can be adapted for use with a variety of water softener tanks without requiring significant modifications to the device.

SUMMARY OF THE INVENTION

The water softener salt tank monitoring device includes multiple sensors capable of determining the level of salt remaining in the tank. The sensors are located in a housing or housings positioned on the exterior of the water softener salt tank. The sensors also include a detection apparatus capable of determining how much salt remains within the water softener salt tank. When the detection mechanism determines that the level of salt within the tank has fallen below a predetermined lower limit, the sensors activate an alarm apparatus that is operably connected to the detection apparatus to provide an audible, visible, electronic communication or combination thereof, to an individual or individuals, indicating the salt in the water softener salt tank needs to be replenished. The alarm mechanism can be formed as a single unit with the detection mechanism in the sensors or can be formed as a separate unit that can be spaced from the sensors. When the alarm mechanism is formed separately and spaced from the sensors, the alarm mechanism can be activated by a signal sent to the alarm mechanism from the sensors.

The detection mechanism for the sensors is an indirect detection mechanism employing a capacitance-based system located in the housing for the sensors. The sensor housing is preferably positioned on the exterior of the water softener tank adjacent a lower limit for the level of the salt within the tank. The detection mechanism then monitors the level of the salt within the tank by obtaining a capacitance measurement on the salt in the tank and using this data to determine whether the amount of salt in the tank has reached the lower limit. At that point, the detection mechanism actuates the alarm mechanism to inform an individual, audibly, visually and/or via electronic communication that the salt within the water softener salt tank needs to be replenished. Electronic communication includes a "push notification" which allows a system, device, or computer to send a notification to another device through a computer network, cellular system, radio, Bluetooth, or wireless network.

The sensors can also be modified to include a separate or second indirect detection mechanism which provides reference data or a reference value to the first indirect detection mechanism to accurately determine the level of the salt within the tank. The reference value provided by the second mechanism can be used by the first mechanism to compare the reference value with an actual value obtained by the first mechanism. If either of the sensors detects the amount of salt in the tank has reached the lower limit, the system can activate the alarm mechanism to inform the individual that the salt level is at or below the lower limit in the tank.

BRIEF DESCRIPTION OF THE DRAWINGS

FIG. 6 is a section view 6-6 of the sensors installed on a brine tank as shown in FIG. 1;

FIG. 7 is a section view 6-6 of the sensors installed on an alternately shaped brine tank;

DESCRIPTION OF THE PREFERRED EMBODIMENT

Figure 1:
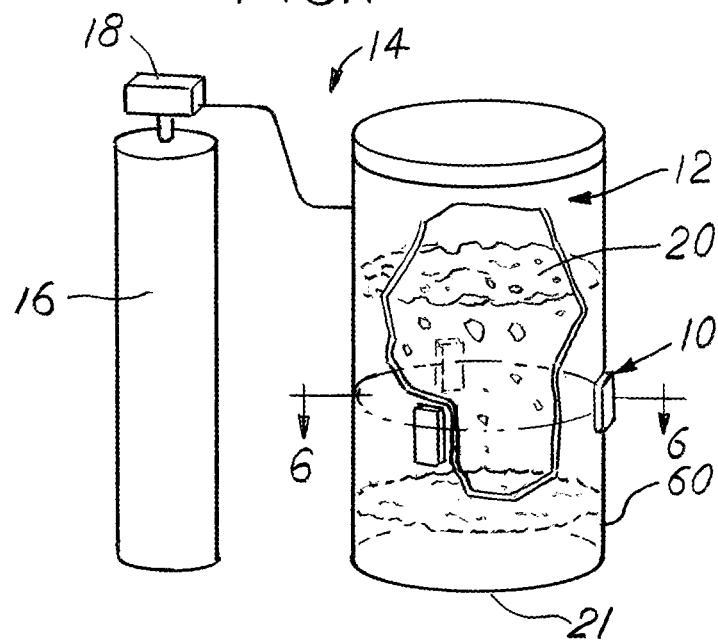
FIG. 1 is an isometric side view of the system as installed on a water softener brine tank.
Figure 2:
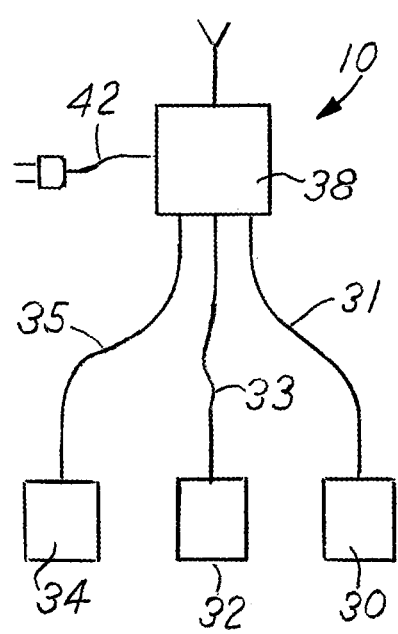
FIG. 2 is a simplified view of the system.
Figure 3:
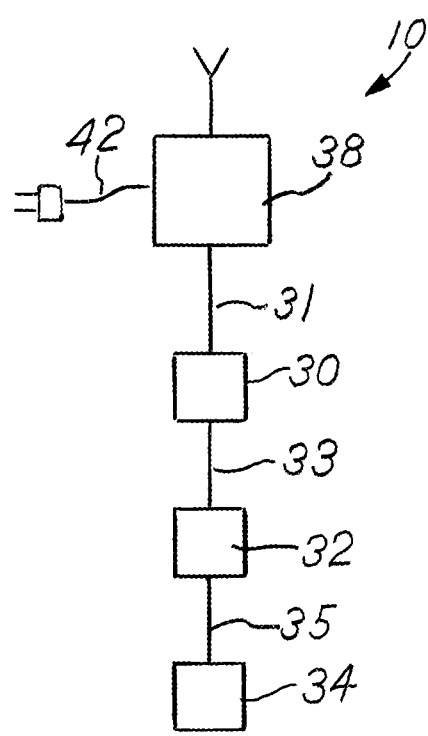
FIG. 3 is a simplified view of an alternate connection the sensors in the system shown in FIG. 2.

A brine tank level monitor 10 is shown installed on a water softener brine tank 12 in FIG. 1. The brine tank 12 is one part of a water softener system 14. The water softener system 14 further includes a resin tank 16 and a regeneration controller 18. The regeneration controller 18 directs water, brine, hard water, and softened water through the system 14. Water softeners are well-known and the detail and theory of their function will not be discussed herein. As the water softener 14 regenerates, it consumes salt 20 from the brine tank 12. The brine tank 12 has a bottom 21 with a perimeter wall 22 that extends upwardly. The bottom 21 and perimeter wall 22 form the receptacle for salt 20. With each regeneration cycle, brine is drawn from the brine tank 12 and is then refilled with water during the regeneration cycle so more brine is ready for the next regeneration cycle. As salt 20 is consumed, the salt level in the brine tank 12 decreases. Once the salt 20 is depleted, the water softener system 14 is no longer effective. The level monitor described herein utilizes at least two capacitive sensors 30, 32, 34, shown in FIG. 2. The capacitive sensors 30, 32, 34 are connected to a controller 38 that is powered either from household mains through a power cord 42, battery (not shown), or other source of power. The controller 38 provides power to the capacitive sensors 30, 32, 34 and receives signals from them through wiring 31, 33, 35. It is contemplated that the controller 38 provides power to the sensors 30, 32, 34 with the sensors chained together with the wiring 31, 33, 35 as shown in FIGS. 2 and 3. It is further contemplated that the controller 38 is integrated into one of the capacitive sensors 30, 32, 34 and the wiring from the other sensors would connect to the sensor that contains the controller 38.

Figure 4:
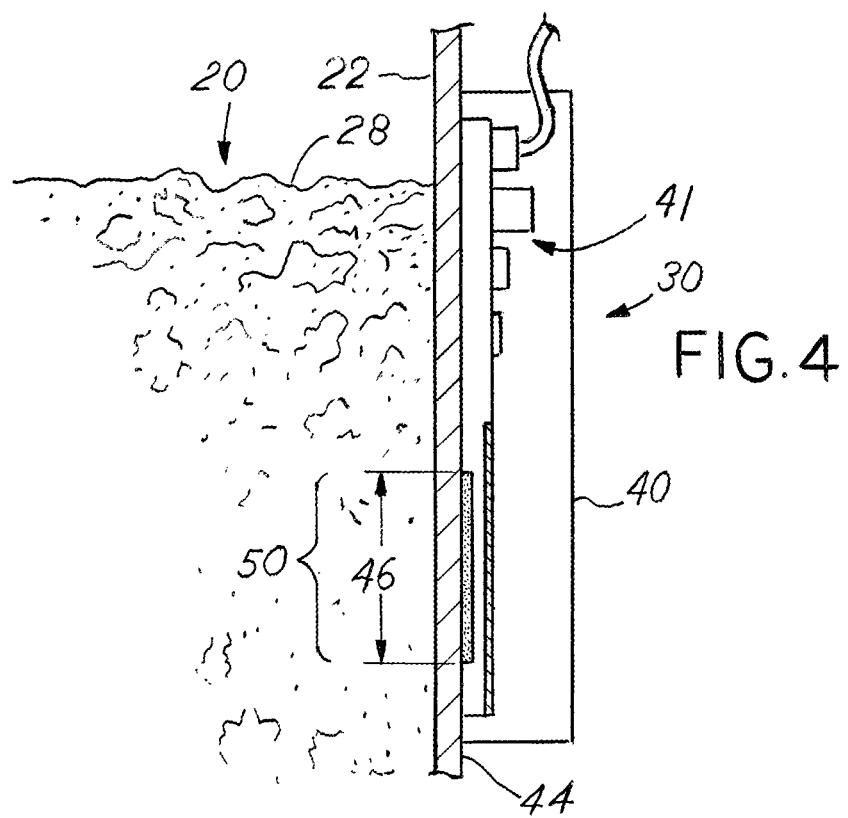
FIG. 4 is a side view of one of the sensors shown in FIG. 1.
Figure 5:
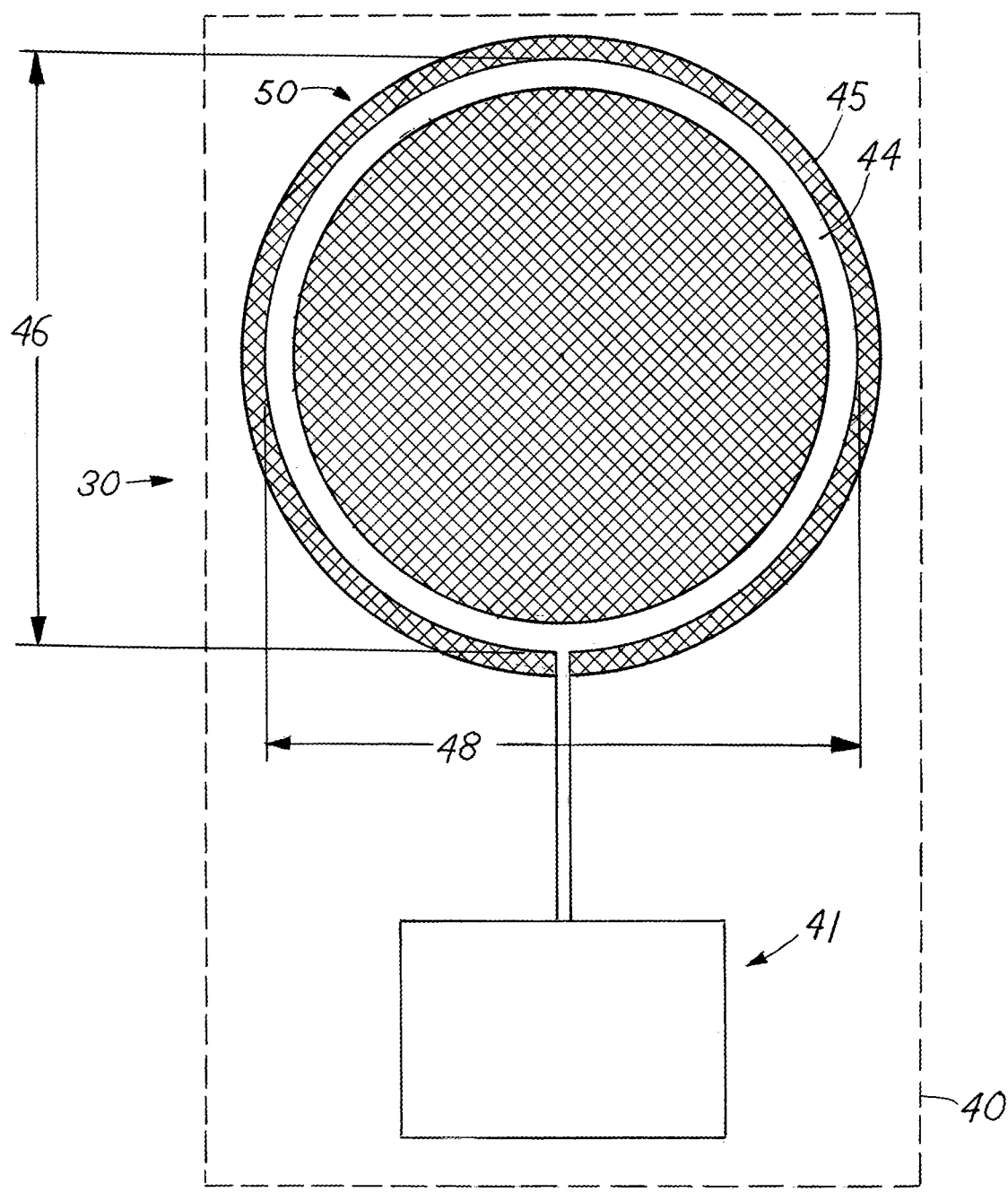
FIG. 5 is a front view of the sensor shown in FIG. 4

The capacitive sensors 30, 32, 34 in the embodiment shown herein are structurally similar or identical; therefore the detail of one sensor 30 will be discussed for simplicity. As shown in FIG. 4, the sensor 30 is encased in a housing 40 to protect the internal components from mechanical damage, liquid intrusion, or tampering. Inside the housing 40 is a sensor board 41 connected to a sensing probe 44. The sensing probe 44 is shown as a conductive trace on a circuit board, but it is contemplated that the probe 44 is a wire that may or may not be integrated with the sensor board 41. The sensing probe 44 has a length 46 and width 48 that determines a sensing area 50 and is affixed to one side of the housing 40. As installed on the brine tank 12, the sensing probe 44 is located close to the perimeter wall 22 to locate the sensing area 50 close to the salt 20. The sensing area 50, as shown in FIGS. 4 and 5, uses a sensing probe 44 shaped as circular ring, but other shapes or dimensions are contemplated. A ground plane 45 overlays the sensing probe 44 to shield the probe 44 from outside interference. Outside interference from external objects placed nearby, animals, or people could cause false triggering or readings. It is contemplated that the capacitive sensors 30, 32, 34 house the sensing probe 44 and the sensor board 41 is integrated into the controller 38. The closer the sensing probe 44 is to the salt 20, the better and more accurate any sensing will be. The sensor or sensing probe 44 may be spaced from the salt 20 by ½" and still detect the presence or absence of salt 20. This allows mounting of the sensors 30, 32, 34 on the outside of the brine tank 12. The brine tank 12, as shown in FIGS. 1, 6, and 8-10, is cylindrical with a central axis 26, but other brine tank shapes are contemplated and the monitor 10 can be used with them. One example is shown in FIG. 7, using the sensors 30, 32, 34 mounted to a rectangular brine tank 13. The sensors 30, 32, 34 are attached or otherwise fixed with respect to the brine tank 12, 13 by an elastic band, adhesive, epoxy, or features integrally formed in the perimeter wall 22. The attaching prevents the sensors from sliding down, being easily knocked out of position, or otherwise being moved. It is contemplated that the sensors could be located in recesses in the perimeter wall 22 of the brine tank.

The sensor 30 operates using a capacitive measurement at the sensing probe 44. The sensor board 41 provides a signal to the sensing probe 44. The sensor board 41 monitors aspects of the signal to determine a capacitance. The sensing probe 44 serves as one plate of a capacitor. Presence, absence, or movement of salt 20 in the brine tank 12 changes the signal. For example, the presence of salt 20 adjacent the sensing probe 44 serves as a virtual second plate, thereby increasing the capacitance read by the sensor board 41. As salt 20 is moved away from the sensing probe 44, the virtual second plate becomes smaller, and therefore the capacitance as measured by the sensor board 41 is reduced. The sensing probe 44 as discussed herein may be mounted vertically, horizontally, or at an angle, depending on the physical properties of the brine tank 12 and measurement properties desired by the user. The sensor board 41 interprets the capacitance reading from the sensor as an analog signal or converts the analog signal to a digital 1 or 0. It then transmits the information to the controller 38 through its wiring 31. The other sensors 32, 34 use capacitive sensing and operate the same as sensor 30.

Figure 8:
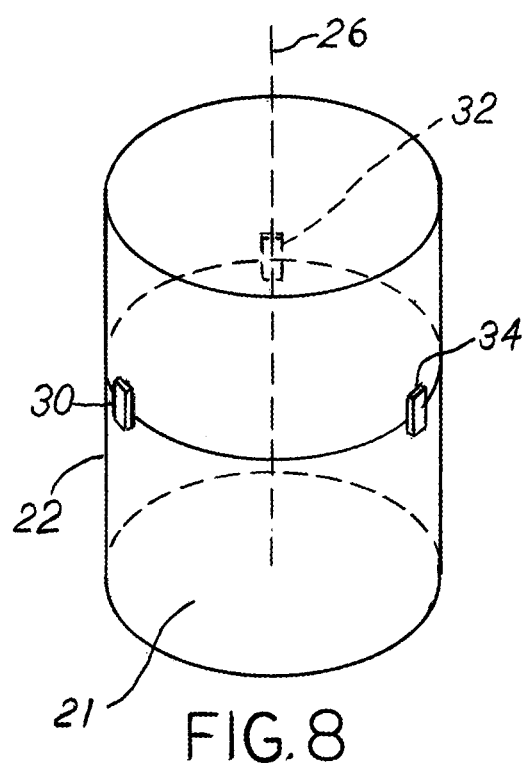
FIG. 8 is an isometric view of the system as installed.
Figure 9:
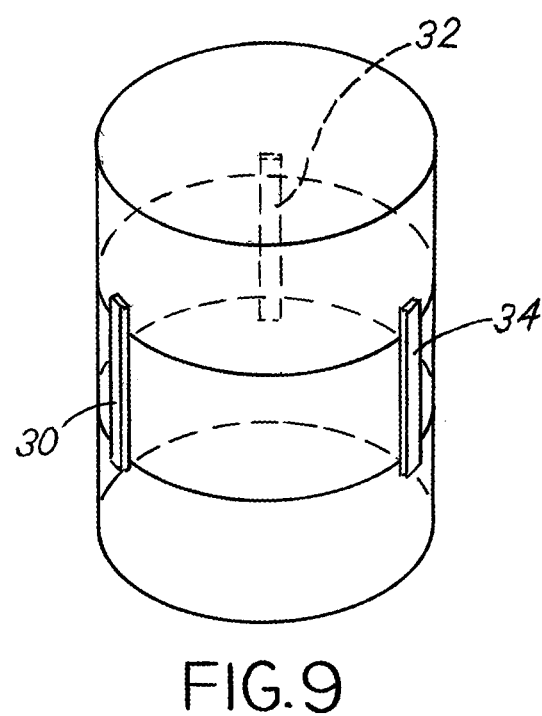
FIG. 9 is an isometric view of an alternate embodiment of the system as installed.

Capacitive sensing is subject to external influence, sometimes causing undesirable operation. The external influence typically comes from the environment, such as a person or animal passing by the sensor, an object being placed next to the sensor, or the sensor being inadvertently bumped or moved. Other influence can come from the regeneration cycle of the water softener system 14, when it adds water to the brine tank 12 to generate more brine. Correspondingly, the influence can come when the water softener system 14 draws brine from the brine tank 12. To combat undesirable influence, additional sensors 32, 34 are located around the circumference or perimeter of the brine tank 12. This is shown in FIG. 4. The sensors 30, 32, 34 are shown at angular positions 52, 54, and 56. When equally spaced on a cylindrical brine tank 12, the sensors 30, 32, 34 are 120 degrees apart. In the event the brine tank is a different shape as the tank 13 depicted in FIG. 7, the sensors 30, 32, 34 can be placed around the perimeter wall 58. While the sensors 30, 32, 34 are shown equally spaced as attached to the perimeter wall 58, it is possible to locate them in other orientations. As shown in FIGS. 1, 8 and 9, the sensors 30, 32, 34 are located at the same elevation on the brine tank 12. Small variations in height are tolerated, particularly since the top surface of the salt is inherently irregular. To prevent undesirable influence from the regeneration of the water softener 14, the elevation of the sensors 30, 32, 34 needs to be above the maximum brine level 60 anticipated in the brine tank 12, based upon the float setting of the brine tank. Locating the sensors too close or at the maximum brine level 60 causes false readings of salt during the regeneration cycle or any time water or brine is at the same elevation of the sensor.

It is contemplated that the capacitive sensors 30, 32, 34 have different features or properties, such as the embodiments shown in FIG. 9. As shown in FIG. 9, the sensors 30, 32, 34 extend vertically. By stretching or extending the sensors 30, 32, 34 vertically, the sensing area 50 for each sensor can be increased. A large sensing area 50 that extends vertically provides a more linear readout by the individual sensor. Alternatively, several sensing areas may be vertically located inside a tall embodiment of the sensor.

The controller 38 receives signals from the capacitive sensors 30, 32, 34. The signals from the sensors are typically a processed signal, however some additional filtering or processing may be necessary to prevent false readings that would be reported to the user. The filtering or processing may be located inside the capacitive sensors 30, 32, 34. The controller 38 takes the signals from each sensor 30, 32, 34 and combines them into a single level reading. The controller 38 may take one or more sensor readings to determine the salt level. The controller may also take the agreement of two sensors assumes that some variation between sensors is tolerated and a tolerance band will be integrated into the sensors 30, 32, 34 or the controller 38. In most cases, the sensors, even when reading a full or completely empty brine tank, will have differences in their individual outputs. The differences can be from manufacturing variations, sensor and mounting variations, environmental variations, or brine tank wall differences (such as wall thickness or tank shape). Regardless of small variations between sensor readings, the sensors will read substantially the same reading when sensing an equivalent salt level that is adjacent each sensor. When two sensors read a substantially equal amount of salt, their outputs are considered substantially equal. Regardless of the variation in the output of the sensors or any tolerance band, the output reading of the sensors between an empty and full state is distinguished by the controller 38.

As the water softener 14 regenerates, it uses a small portion of salt 20 from the brine tank 12, making the level go down a small amount with each regeneration cycle. The salt 20 has a top surface 28 that is irregular and changes as the salt is consumed. As the top surface 28 approaches the sensing area 50, the capacitance as read by the sensors 30, 32, 34 begins to drop. The largest change in the capacitance occurs as the top surface 28 moves past the sensing area 50. Because the top surface 28 is irregular, one of the sensors 30, 32, 34 will likely register the drop in capacitance before the other sensors from the salt level being lower at that sensor. When one of the sensors reads significantly differently from the others, the different reading may be acted upon or may be ignored by the controller 38. As the salt 20 continues to be consumed and the top surface 28 passes the sensing area 50 of a second sensor, two sensors report a low salt condition to the controller 38. Once two sensors report a low salt condition, the controller 38 confirms a low level. Depending on whether the system is set up to determine a low level of salt by one sensor, or use two or more sensors, the controller will register that the salt level in the brine tank 12 is low and report this to the user. The low salt condition may be reported via lights or an audible alarm. The lights and/or audible alarm may be integrated with the controller 38 or be remotely located.

In order to electronically communicate with the user, the controller 38 connects to the user's home network, commonly over a wireless network. Wired network capability may be provided as an alternate or supplement to wireless network communication. In remote locations, where a wireless or wired network is not available, it is contemplated that the controller 38 includes cellular or point-to-point RF wireless communication protocol. The controller 38 uses the network as a conduit to send an email, text, or push notification using an application that may be downloaded onto the user's mobile device. The controller 38 may have a web server built in that provides a user interface, where the user can change settings. Optionally, the controller 38 can connect to a mobile or other computing device through Bluetooth.

The controller reports the salt level in the tank if the measured level is below the threshold level. The threshold level may be adjustable by the user, either through programming or by relocating the sensor(s).

The push notification, SMS, MMS, or message to the user can include retailers or specific brand recommendations, based on the user's softener system and user preferences. The system may be set to remind the user at specific times, based on the user's schedule or preferences. The system may provide a recurring notification to remind the user daily, weekly, or on another interval while the system is low on salt. Further, the system can be configured to automatically schedule a delivery of salt through a provider, retailer, or other replenishment service.

It is understood that while certain aspects of the disclosed subject matter have been shown and described, the disclosed subject matter is not limited thereto and encompasses various other embodiments and aspects. No specific limitation with respect to the specific embodiments disclosed herein is intended or should be inferred. Modifications may be made to the disclosed subject matter as set forth in the following claims.

What is claimed is:

1. A device for monitoring a salt level in a water softener brine tank having a perimeter wall extending upwardly from a bottom and having a maximum brine level, said device comprising:
    a first capacitive sensor located at a first position on an outside surface of said perimeter wall of said brine tank and spaced from said bottom at a first distance, a second capacitive sensor located at a second position on said perimeter wall and spaced at a second distance from said bottom, and a third capacitive sensor located at a third position on said perimeter wall and spaced at a third distance from said bottom, said first, second, and third distances being above said maximum brine level;
    each said capacitive sensor having a corresponding sensing probe located between said perimeter wall and a shield, said shield overlaying said sensing probe, each said capacitive sensor having a corresponding output, said corresponding output movable between a salt absent reading and a salt present reading, said absent reading defined by a capacitance reading corresponding to said salt level being below said sensing probe, said present reading defined by said capacitance reading corresponding said salt level being overlaid by said sensing probe;
    each said sensor communicating with a controller, said controller reading said corresponding outputs from each said capacitive sensor, said controller comparing said outputs from said first, second, and third capacitive sensors;
    said controller reporting a low salt condition when at least two of said outputs of said capacitive sensors read said salt absent reading.

2. The device according to claim 1, said controller connected to a computer network, said reporting of said low salt condition occurring over said network.

3. The device according to claim 2, said reporting includes a recurring push notification while said low salt condition exists.

4. The device according to claim 1, wherein said first, second, and third positions are substantially equally spaced around said perimeter wall.

5. The device according to claim 1, wherein said first, second, and third distances are at substantially equal vertical positions on said perimeter wall.

6. A method of monitoring a salt level in a water softener brine tank, said brine tank having a perimeter wall extending from a bottom, said method comprising:

providing a first, second, and third capacitive sensor, each said sensor having a sensing probe;

providing a controller in communication with said sensors;

attaching said first, second, and third capacitive sensors on an outside surface of said perimeter wall with each said sensing probe above a maximum brine level;

said controller monitoring and comparing outputs of said capacitive sensors;

said controller converting said outputs of said capacitive sensors into a value between a salt present or salt absent value; and reporting a low salt condition when at least one of said capacitive sensor values have a salt absent value.

7. The method according to claim 6, wherein said reporting of said low salt condition generates a visual or audible alert.

8. The method according to claim 6, wherein said reporting of said low salt condition occurs wirelessly from said controller.

9. The method according to claim 8, wherein said reporting occurs through a push notification.

10. The method according to claim 9, wherein said reporting is recurring while said low salt condition is reported by said controller.

11. A device for monitoring a salt level in a water softener brine tank having a perimeter wall extending upwardly from a bottom and having a maximum brine level, said device comprising:

a first capacitive sensor located at a first position on an outside surface of said perimeter wall of said brine tank and spaced from said bottom at a first distance, a second capacitive sensor located at a second position on said perimeter wall and spaced at a second distance from said bottom, and a third capacitive sensor located at a third position on said perimeter wall and spaced at a third distance from said bottom, said first, second, and third distances being above said maximum brine level, each said capacitive sensor having a corresponding sensor probe;

each said capacitive sensor having a corresponding output, said corresponding output movable between a salt absent reading and a salt present reading, said absent reading defined by said salt level being below said sensor probe, said salt present reading defined by said salt level being above said sensor probe; and when at least two of said capacitive sensors substantially agree, a controller reporting said output.

12. The device according to claim 11, said controller connected to a computer network, said reporting occurring over said network.

13. The device according to claim 12, said reporting includes a recurring push notification while said salt level being below at least two of said sensor probes.

14. The device according to claim 11, wherein each said sensing probe having a corresponding shield overlaying a sensing probe to place said sensing probe between said perimeter wall and said shield.

15. The device according to claim 11, wherein said first, second, and third positions are substantially equally spaced around said perimeter wall.

16. The device according to claim 11, wherein said first, second, and third distances are at substantially equal vertical positions on said perimeter wall.

17. The method according to claim 11, when said output corresponds to a salt absent condition, said controller generates a visual or audible alert.

18. The method according to claim 11, wherein said reporting occurs through a push notification.

* * * * *